United States Patent
Brodfuehrer et al.

(10) Patent No.: US 6,353,122 B1
(45) Date of Patent: Mar. 5, 2002

(54) METHOD FOR EPOXIDATION OF 3-METHYLENECYCLOPROPANES

(75) Inventors: Paul R. Brodfuehrer, Syracuse; Thomas R. Sattleberg, Sr., Cicero, both of NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/018,425

(22) Filed: Feb. 4, 1998

Related U.S. Application Data

(60) Provisional application No. 60/038,990, filed on Feb. 26, 1997.

(51) Int. Cl.$^7$ .................. C07D 301/02; C07C 45/00
(52) U.S. Cl. .................................. 549/518; 568/338
(58) Field of Search ................... 549/518; 568/338

(56) References Cited

U.S. PATENT DOCUMENTS

| | | | |
|---|---|---|---|
| 5,064,961 A | 11/1991 | Bisacchi et al. | 544/276 |
| 5,237,096 A | 8/1993 | Godfrey et al. | 562/506 |
| 5,773,614 A | 6/1998 | Godfrey et al. | 544/276 |

OTHER PUBLICATIONS

J.K. Crandall and W.W. Conover, "Peracid Oxidation of Methylenecyclopropanes", *J. Org. Chem.*, 43 (18), pp.3533–3535 (1978).

C.–N. Hsiao and S.M. Hannick, "Efficient Synthesis of Protected (2S,3S)–2,3–BIS (Hydroxymethyl)Cyclobutanone, Key Intermediates for the Synthesis of Chiral Carbocyclic Analogues of Oxetanocin", *Tet. Letters*, 31 (46), pp.6609–6612 (1990).

J.R. Salaün and J.M. Conia, *Chem. Comm.*, pp. 1579–1580 (1971).

*Primary Examiner*—Amelia Owens
(74) *Attorney, Agent, or Firm*—Aldo A. Algieri

(57) ABSTRACT

The present invention provides a process for the expoxidation of a protected 3-methylene-(trans)-1,2,-hydroxymethylcyclopropane with cyclohexanone and potassium peroxymonosulfate and subsequent rearrangement to provide the corresponding cyclobutanone.

11 Claims, No Drawings

METHOD FOR EPOXIDATION OF 3-METHYLENECYCLOPROPANES

CROSS-REFERENCE TO RELATED APPLICATIONS

This nonprovisional application claims the benefit of copending provisional application, U.S. Ser. No. 60/038,990 filed Feb. 26, 1997.

BACKGROUND OF THE INVENTION

Cyclobutyl carbocyclic nucleosides have recently been found to have potent biological activity. Among these is the antiviral agent of the Formula I

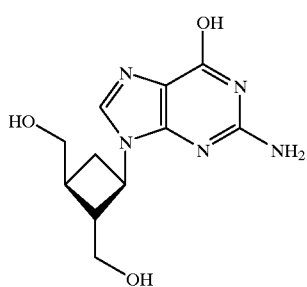

I which is active against herpes simplex virus type I and 2, varicella zoster virus, human cytomegalovirus, vaccina virus, murine leukemia virus and human immunodeficiency virus.

A number of successful syntheses of the antiviral agent of Formula I have been described using the protected trans-2,3-bis (hydroxymethyl)-cyclobutanones of Formula II as a key intermediate

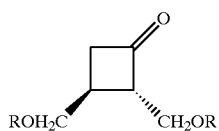

II wherein R is a protecting group. Norbeck, D. W., et al., in European Patent Application 366,059 published May 2, 1990, describe the preparation of purinyl and pyrimidinyl antiviral agents including the compound of Formula I by several synthetic routes using the intermediate of Formula II. Bisacchi, G. S., et al., in U.S. Pat. No. 5,064,961, issued Nov. 12, 1991, also disclose a process for the preparation of the antiviral compound of Formula I using a key intermediate of Formula II.

The most useful method for the preparation of this key intermediate is from a protected-(trans)-1,2-hydroxymethylcyclopropane of Formula IIII

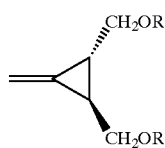

III wherein R is a protecting group which through a series of standard transformations is prepared from Feist's acid. The conversion of a compound of Formula IIII by epoxidation with m-chloroperoxybenzoic acid (m-CPBA) to the intermediate epoxide and subsequent ring expansion to a cyclobutanone of Formula II by treatment with catalytic lithium iodide was described by Hsiao, C.-N., et al., Tetrahedron Lett., 31, 6609 (1990) and Godfrey, Jr., J. D., et al., U.S. Pat. No. 5,237,096 (1993).

Organic peroxyacids, in general, have been successfully used for the epoxidation of methylenecyclopropanes to their respective oxaspiropentanes, generally followed by isomerization to cyclobutanone. Conia, J. M., et al., Chem. Comm., 1579 (1971) prepared cyclobutanone in high yield by epoxidation of methylenecyclopropane with p-nitroperbenzoic acid in methylene chloride followed by rearrangement with catalytic LiI. Crandall, J. K., et al., in J. Org. Chem., 43, 3533 (1978) also described the epoxidation and rearrangement of substituted methylenecyclopropanes using m-CPBA, a more commonly used reagent. These authors also noted that the presence of substituent ester groups on the cyclopropane ring significantly deactivated the double bond toward epoxidation with p-nitroperbenzoic acid.

Although the prior art method works reasonably well on a small scale, a number of problems were encountered on a larger scale in the m-CPBA epoxidation of the compound of Formula III. In order to achieve a reasonable reaction rate, the reaction is run fairly concentrated in methylene chloride. The by-product m-chlorobenzoic acid (m-CBA) precipitates out and must be removed by filtration. In addition, under prolonged reaction time, opening of the epoxide by m-CBA acid to give significant amounts of the benzoate ester was observed and the amount of the benzoate side product was difficult to control. Furthermore, the epoxidation did not go to completion with the preferred benzoyl protecting group, even after prolonged reaction for over 24 hours. The workup was also quite tedious, as excess m-CPBA needs to be quenched and the resulting m-CBA removed prior to proceeding with the rearrangement step. Thus, there is a need for a method which does not produce by-products, avoids long reaction times, is economical and easy to handle and which would be suitable for larger scale production.

SUMMARY OF THE INVENTION

The present invention provides an improved method for converting methylenecyclopropanes to cyclobutanones via an intermediate cyclopropyl epoxide using a mixture of cyclohexanone and potassium peroxymonosulfate. The method is simple, inexpensive, and amenable to large scale preparation of the cyclobutanones of Formula II

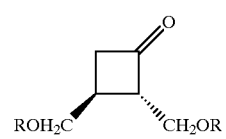

II wherein R is a hydroxy-protecting group.

DETAILED DESCRIPTION OF THE INVENTION

The present invention relates to the epoxidation of a protected 3-methylene-(trans)-1,2-hydroxymethylcyclopropanes of the Formula III with a mixture of cyclohexanone and potassium peroxymonosulfate and subsequent rearrangement with lithium iodide or lithium bromide to provide a cyclobutanone of Formula II as illustrated in Reaction Scheme 1.

The term "hydroxy-protecting group" refers to those groups well-known to those skilled in the art which can be employed in the present invention to block or protect the hydroxyl group. Preferably, said groups can be removed, if desired, by methods which do not result in any appreciable destruction of the remaining portion of the molecule, for example, by chemical or enzymatic hydrolysis, treatment with chemical reducing agents under mild conditions, irradiation with ultraviolet light or catalytic hydrogenation.

Suitable hydroxy-protecting groups include acyl groups such as acetyl, propionyl, butyryl, chloroacetyl, dichloroacetyl and trichloroacetyl, phenoxycarbonyl, benzyloxycarbonyl, benzhydryloxycarbonyl, trityloxycarbonyl, p-nitro-benzyloxycarbonyl and 2,2,2-trichloroethoxy-carbonyl; aroyl groups such as benzoyl and substituted benzoyl, for example, methoxybenzoyl, nitrobenzoyl, methylbenzoyl and the like; alkyl groups such as methoxymethyl, benzyloxymethyl, allyl; aralkyl groups such as benzyl, benzhydryl, trityl or p-nitrobenzyl; or triorganosilyl groups such as tri($C_1$–$C_6$)alkylsilyl (e.g. trimethylsilyl, triethylsilyl, triisopropylsilyl, isopropyidimethylsilyl, t-butyidimethylsilyl, methyidiisopropylsilyl or methyidi-t-butylsilyl), triarylsilyl (e.g. triphenyl-silyl, tri-p-xylsilyl) or triaralkylsilyl (e.g. tribenzylsilyl). Examples of these and other suitable hydroxy-protecting groups and methods for their formation and removal are known in the art, e.g. see Protective Groups in Organic Synthesis, T.W. Greene, John Wiley & Sons, New York, 1991, Chapter 2, and references therein.

Preferred hydroxy-protecting groups are bulky triorganosilyl groups such as triisopropylsilyl, t-butyldiphenylsilyl or t-butyldimethyl-silyl; aroyl groups such as benzoyl and substituted benzoyl and aryl groups such as benzyl and substituted benzyl.

SCHEME 1

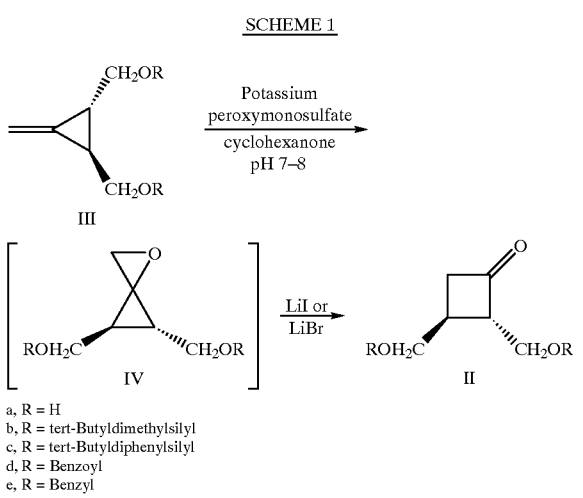

a, R = H
b, R = tert-Butyldimethylsilyl
c, R = tert-Butyldiphenylsilyl
d, R = Benzoyl
e, R = Benzyl According to the process of this invention, a cyclopropane of Formula IIIb–IIIe is dissolved in a mixture of cyclohexanone with or without an inert organic solvent, such as ethyl acetate, butyl acetate, dichloromethane, 1,2-dichloroethane, chloroform, tetrahydrofuran, dioxane, 1,2-dimethoxyethane and the like, and aqueous pH 7.5 phosphate buffer. An aqueous solution of potassium peroxymonosulfate which is commercially available under the trade name (Oxone®) as a mixture of the formula $2KHSO_5 \cdot KHSO_4 \cdot K_2SO_4$ is added to the mixture over a period of 2–10 hours. The temperature of the mixture is maintained at about 0–25° C. and the pH is maintained at about 7–8 with aqueous KOH. Conversion to the corresponding epoxide of Formula IVb-IVe is generally complete with 2–4 equivalents of potassium peroxymonosulfate relative to substrate. The epoxide of Formula IV is advantageously isolated by separating the phases and extracting the aqueous phase with an organic solvent, preferably ethyl acetate or methylene chloride. Concentration of the combined organic solution gives the crude epoxide of Formula IV in essentially quantitative yield.

The crude epoxide of Formula IV may be dissolved in an inert organic solvent and treated with catalytic LiI or LiBr or, alternatively, catalytic LiI or LiBr may be added to the epoxide rich organic solution at 0–5° C. to effect rearrangement to the cyclobutanone of Formula II within 5–10 minutes. The desired cyclobutanone is advantageously isolated by concentrating to a residue and crystallizing from an appropriate organic solvent, such as isopropanol or, in some cases, addition of water to precipitate the product as a crystalline solid.

In the process of the present invention, the in situ generation of 1,2-dioxaspiro[2.5]octane using cyclohexanone and potassium peroxymonosulfate is especially preferred. The cyclopropane of Formula IIIc is epoxidized to the compound of Formula IVc in quantitative yield with only 2–4 equivalents of potassium peroxymonosulfate. The same results were obtained with the conversion of the compound of Formula IIId to the epoxide of Formula IVd, which was even more surprising, since in this series the benzoyl hydroxy protection is known to deactivate the double bond toward epoxidation. The application of the in situ dioxirane generation method using cyclohexanone in a two phase system without the use of phase transfer catalyst is unique. The yields are nearly quantitative and the process is economical and amenable to large scale epoxidations.

As taught by Bisacchi, G. S., et al., in U.S. Pat. No. 5,064,961, the cyclobutanone intermediate of Formula II is first treated with lithium trisiamylborohydride and then with tosyl chloride to give the cyclobutane compound of formula V.

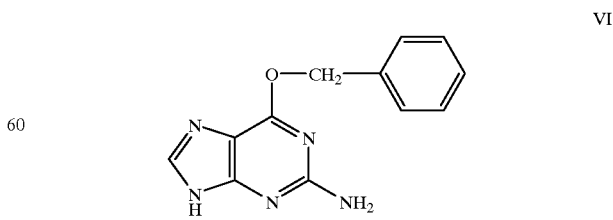

The tosyl compound of Formula V is then treated with benzyloxy guanine of the formula VI and,

VI after removal of the protecting groups, the antiviral agent of formula I is produced.

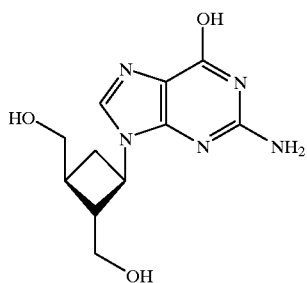

DESCRIPTION OF SPECIFIC EMBODIMENTS

The methods which constitute this invention and the compounds prepared will appear more fully from a consideration of the following examples which are given for the purpose of illustration only and are not to be construed as limiting the invention in sphere or scope.

In the following examples, all temperatures are given in degrees Centigrade. Melting points were recorded on a capillary melting point apparatus and the temperatures are uncorrected. Proton magnetic resonance ($^1$H NMR) spectra were recorded on a Bruker AM-360 spectrometer. All spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet.

EXAMPLE 1

(4S-trans)-1-Oxaspiro[2.2]pentane-5,5-dimethanol, Dibenzoate Ester

A 2 L round bottom flask was charged with (1R-trans)-3-methylene-1,2-cyclopropanedimethanol, dibenzoate ester [prepared by the general procedures described by Bisacchi, G. S., et al., *J. Med. Chem.*, 34, 1415, (1991) and Godfrey, Jr., J. D., et al., U.S. Pat. No. 5,237,096 (1993)] (25.0 g, 77.6 mmol), cyclohexanone (129 mL), and phosphate buffer (1.0 g of sodium phosphate dibasic and 50 mg of disodium EDTA in 50 mL of water). The mixture was cooled to 15° C. and stirred vigorously with a mechanical stirrer. To this mixture was added a solution of potassium peroxymonosulfate (Oxone®) (190.8 g. 310 mmol) and disodium EDTA (50 mg), in water (600 mL) dropwise during 3.5 h, maintaining the temperature at about 20°C during the addition. The pH was maintained at 7.3–7.5 by autotiration with 3N KOH (300 mL) during the addition. HPLC indicated the reaction was complete at the end of the addition. The reaction mixture was transferred to a separatory funnel with EtOAc (50 mL). The phases were separated and the aqueous phase was extracted with additional EtOAc (100 mL). The combined organic solution was dried over Na$_2$SO$_4$ and concentrated in vacuo to a volume of about 200 mL. This solution containing the title compound was generally used directly in the conversion to the corresponding cyclobutanone. The title compound could be isolated by concentrating the above solution in vacuo to a residue.

$^1$H NMR (CDCl$_3$): δ 1.90 (1H, m), 3.18 (1H, d, J=8.0 Hz), 3.19 (1H, d, J=7.7 Hz), 4.14 (1H, dd, J=8.1, 11.7 Hz), 4.22 (1H, dd, J=8.3, 11.7 Hz), 4.33 (1H, dd, J=6.1, 11.7 Hz), 4.43 (1H, dd, J=5.9, 11.7), 7.20 (4H, m), 7.39 (2H, m), 7.81 (4H, m)

EXAMPLE 2

(2S-trans)-2,3-Bis[(benzoyloxy)methyl]cyclobutanone

The solution of (4S-trans)-1-oxaspiro[2.2]pentane-5,5-dimethanol, dibenzoate ester prepared in Example 1 was cooled to 0–5° C. and LiBr (680 mg, 7.8 mmol) was added. An exotherm to 20° C. was observed. After stirring for 10 minutes, HPLC indicated the reaction was complete. The reaction mixture was concentrated in vacuo to remove most of the EtOAc and diluted with water (330 mL). The mixture was cooled to 0° C. as the product began to crystallize. The crystal slurry was stirred at 0° C. for 16 h then filtered. The filter cake was washed with water (50 mL) and dried to constant weight in vacuo at 20° C. to give 26.5 g (100%) of crude title compound as a white crystalline solid. A 5 g sample of this material was recrystallized from MeOH (50 mL) to give 3.36 g of purified title compound: mp=97–98° C. $^1$H NMR (CDCl$_3$):δ2.97 (1H, m), 3.07 (1H, ddd, J=3.0, 7.2, 17.6Hz), 3.25 (1H, ddd, J=2.5, 9.4, 17.6 Hz), 3.66 (1H, m), 4.58 (4H, m), 7.42 (4H, m), 7.56 (2H, m), 8.00 (m, 4H)

EXAMPLE 3

(4S-trans)-1-Oxaspiro[2.2]pentane-4,5-dimethanol, di t-butyidiphenylsilyl Ether

A 1 L round bottom flask was charged with (1R-trans)-3-methylene-1,2-cyclopropanedimethanol, di t-butyldiphenylsilyl ether (25.0 g, 42.3 mmol) [prepared according to the general procedure of Hsiao, C.-N., et al., *Tetrahedron Lett.*, 31, 6609 (1990)], cyclohexanone (80 mL), and phosphate buffer (1.3 g of sodium phosphate dibasic and 50 mg of disodium EDTA in 50 mL of water). The mixture was heated to 30° C. and stirred vigorously with a mechanical stirrer. To this mixture was added a solution of potassium peroxymonosulfate (Oxone®) (104.5 g, 170 mmol) and disodium EDTA (50 mg) in water (350 mL) dropwise during 4.5 h while maintaining the temperature at about 30° C. during the addition. The pH was maintained at 7.3–7.5 by autotitration of 3 N KOH (158 mL) during the addition. The reaction was complete after 15 minutes as ascertained by HPLC. The reaction mixture was filtered through a celite pad, which was washed with EtOAc (100 mL). The two phase filtrate was separated and the aqueous phase was extracted with additional EtOAc (150 mL). The organic phases were combined and washed with saturated NaHCO$_3$ (150 mL), dried over anhydrous sodium sulfate, and concentrated in vacuo to a volume of about 100 mL. This solution containing the title compound was generally used directly in the conversion to the corresponding cyclobutanone. The title compound could be isolated by concentrating the above solution in vacuo to a residue.

$^1$H NMR (CDCl$_3$): δ 0.87 (9H, s), 0.88 (9H, s), 1.50 (1H, m), 2.92 (1H, d, J=17.1 Hz), 2.94 (1H, d, J=16.7 Hz), 3.55 (2H, d, J=5.9 Hz), 3.61 (1H, dd, J=7.0, 11.1 Hz), 3.71 (1H, dd, J=6.3, 10.8 Hz), 7.20 (12H, m), 7.50 (8H, m)

EXAMPLE 4

(2S-trans)-2,3-Bis[t-butyldiphenylsilyloxy)methyl]-cyclobutanone

The solution of (4S-trans)-1-oxaspiro[2.2]pentane-4,5-dimethanol, di t-butyldiphenylsilyl ether prepared in Example 3 was cooled to 0° C. and LiI (1.14 g, 8.5 mmol) was added. After 15 minutes HPLC indicated the reaction was complete. The dark amber reaction mixture was washed with a 1:1 mixture of saturated $Na_2S_2O_3$ and water (2×100 mL). The combined aqueous phase was extracted with EtOAc (50 mL), and the combined organic solution washed with saturated $Na_2S_2O_3$ (50 mL). The combined organic phase was concentrated in vacuo to remove EtOAc. A 3:1 mixture of water and 1-butanol (100 mL) were added and concentrated in vacuo to azeotrope out most of the cyclohexanone and give 31 g of crude title compound as a viscous oil. NMR analysis of this material showed it to consist of the desired product and residual cyclohexanone. This material was crystallized from MeOH/water (200 mL) to give 18.37 g (72% yield from the starting material of Example 3) of purified title compound as an off-white crystalline solid: mp=43–450° C.

$^1$H NMR (CDCl$_3$): δ 0.95 (9H, S), 0.97 (9H, S), 2.76 (1H, m), 2.84 (2H, m), 3.22 (1H, m), 3.61 (1H, dd, J=4.0, 10.4 Hz), 3.78 (2H, m), 3.89 (1H, dd, J=4.0, 10.4 Hz), 7.33 (12H, m), 7.56 (8H, m)

EXAMPLE 5

(4S-trans)-1-Oxaspiro[2.2]pentane-5.5-dimethanol, dibenzoate ester

A 1 L round bottom flask was charged with (1R-trans)-3-methylene-1,2-cyclopropanedimethanol,dibenzoate ester [prepared by the general procedures described by Bisacchi, G. S., etal.*J. Med. Chem.*, 34, 1415, (1991) and Godfrey, Jr., J. D. et al., U.S. Pat. No. 5,237,096 (1993)] (20.0 g, 62 mmol), cyclohexanone (64.3 mL, 620 mmol, 10 equiv), ethyl acetate (35 mL) and phosphate buffer (1.0 g of sodium phosphate dibasic in 40 mL of water). The mixture was cooled to 0° C. and stirred vigorously with a mechanical stirrer. To this mixture was added a solution of potassium peroxymonosulfate (Oxone®) (76.2 g, 124 mmol) in water (300 mL) dropwise during 8.5 h, maintaining the temperature at about 0° C. during the addition. The pH was maintained at 7.3–7.5 by autotitration with 4N NaOH (86 mL) during the addition. The mixture was vigorously stirred for 15 h at 0° C., at which time HPLC indicated the reaction was complete. The reaction mixture was transferred to a separatory funnel. The phases were separated and the aqueous phase was extracted with EtOAc (100 mL). The combined organic solution was dried over $Na_2SO_4$ and concentrated in vacuo to a volume of about 150 mL. This solution containing the title compound was generally used directly in the conversion to the corresponding cyclobutanone. The title compound could be isolated by concentrating the above solution in vacuo to a residue, which is identical to the compound of Example 1.

EXAMPLE 6

(4S-trans)-1-Oxaspiro[2.2]pentane-5.5-dimethanol, dibenzoate ester

A 500 mL round bottom flask was charged with (1R-trans)-3-methylene-1,2-cyclopropanedimethanol,dibenzoate ester [prepared by the general procedures described by Bisacchi, G. S., et al. *J. Med. Chem.*, 34, 1415, (1991) and Godfrey, Jr., J. D. et al., U.S. Pat. No. 5,237,096 (1993)] (5.0 g, 15.5 mmol), cyclohexanone (12.8 mL, 124 mmol, 8 equiv), ethyl acetate (12 mL) and phosphate buffer (0.25 g of sodium phosphate dibasic in 10 mL of water). The mixture was cooled to 0° C. and stirred vigorously with a mechanical stirrer. To this mixture was added a solution of potassium peroxymonosulfate (Oxone®) (19.0 g, 31 mmol) in water (75 mL) dropwise during 6.5 h, maintaining the temperature at about 0° C. during the addition. The pH was maintained at 7.3–7.5 by autotitration with 4N NaOH (21 mL) during the addition. The mixture was vigorously stirred for 15 h at 0° C., at which time HPLC indicated incomplete reaction, with 5% unreacted starting material remaining and 10% decomposition products. The reaction mixture was transferred to a separatory funnel with EtOAc (30 mL). The phases were separated and the aqueous phase was extracted with EtOAc (50 mL). The combined organic solution was dried over $Na_2SO_4$ and concentrated in vacuo to a volume of about 80 mL. This solution containing the title compound was generally used directly in the conversion to the corresponding cyclobutanone. The title compound could be isolated by concentrating the above solution in vacuo to a residue, which is identical to the compound of Example 1.

What is claimed is:

1. A process for the preparation of a compound of Formula IV

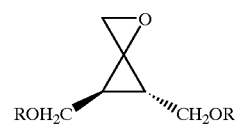

IV wherein R is a hydroxy-protecting group which comprises reacting a compound of the Formula III

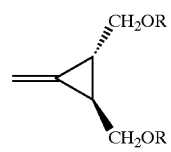

III wherein R is a hydroxy-protecting group in cyclohexanone or in a mixture of cyclohexanone and an inert organic solvent with an aqueous buffered solution containing potassium peroxymonosulfate to produce an epoxide of Formula IV wherein R is a hydroxy-protecting group.

2. A process of claim 1 further comprising treating the epoxide of Formula IV as defined in claim 1, in an organic solvent with lithium iodide or lithium bromide to produce a compound of Formula II

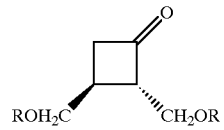

II wherein R is a hydroxy-protecting group.

3. A process of claim 1 wherein R is benzoyl, benzyl, t-butyldiphenylsilyl or t-butyldimethylsilyl.

4. A process of claim 2 wherein R is benzoyl, benzyl, t-butyldiphenylsilyl or t-butyldimethylsilyl.

5. A process of claim 1 wherein R is benzoyl.

6. A process of claim 2 wherein R is benzoyl.

7. A process of claim 1 wherein R is t-butyldiphenylsilyl.

8. A process of claim 1 wherein said buffered solution is maintained at a pH of about 7.0–8.0.

9. A process of claim 8 wherein the pH is about 7.3–7.5.

10. A process of claim 1 wherein the organic solvent is ethyl acetate.

11. A process of claim 1 wherein the amount of potassium peroxymonosulfate is about 2–4 equivalents.

* * * * *